US008457720B2

(12) United States Patent
Leiblein et al.

(10) Patent No.: US 8,457,720 B2
(45) Date of Patent: Jun. 4, 2013

(54) APPARATUS FOR ASSISTING WITH THE POSITIONING OF AN IMPLANT

(75) Inventors: Rudolf Leiblein, Weisendorf (DE); Martin Spahn, Erlangen (DE)

(73) Assignee: Siemens Aktiengesellschaft, München (DE)

( * ) Notice: Subject to any disclaimer, the term of this patent is extended or adjusted under 35 U.S.C. 154(b) by 481 days.

(21) Appl. No.: 12/754,691

(22) Filed: Apr. 6, 2010

(65) Prior Publication Data

US 2010/0256510 A1    Oct. 7, 2010

(30) Foreign Application Priority Data

Apr. 6, 2009    (DE) .......................... 10 2009 016 482

(51) Int. Cl.
*G03B 42/02*    (2006.01)

(52) U.S. Cl.
USPC .......................................................... 600/427

(58) Field of Classification Search
None
See application file for complete search history.

(56) References Cited

U.S. PATENT DOCUMENTS

| | | | |
|---|---|---|---|
| 5,586,201 A | 12/1996 | Whiting et al. | |
| 5,779,672 A * | 7/1998 | Dormandy, Jr. | ........... 604/99.04 |
| 8,000,507 B2 * | 8/2011 | Rongen et al. | ................. 382/128 |
| 2004/0260175 A1 | 12/2004 | Florent et al. | |
| 2005/0182319 A1 * | 8/2005 | Glossop | ......................... 600/424 |
| 2006/0058647 A1 | 3/2006 | Strommer et al. | |
| 2008/0045827 A1 | 2/2008 | Rongen et al. | |
| 2008/0267475 A1 | 10/2008 | Lendl | |

FOREIGN PATENT DOCUMENTS

| | | |
|---|---|---|
| CA | 2559340 A1 | 3/2007 |
| DE | 69133195 T2 | 10/2003 |
| DE | 102007013624 A1 | 9/2008 |
| WO | WO 2003043516 A2 | 5/2003 |
| WO | WO 2005104951 A1 | 11/2005 |
| WO | WO 2008041154 A2 | 4/2008 |
| WO | WO 2008050316 A2 | 5/2008 |
| WO | 102007019328 A1 | 11/2008 |

* cited by examiner

*Primary Examiner* — Jacqueline Cheng

(57) ABSTRACT

An apparatus for assisting with positioning of an implant on a specific point in a vessel of a patient is proposed. A first interventional instrument is inserted in a region of the specific point. A series of 2D x-ray recordings of the vessel with the first instrument are obtained by adjusting an x-ray device. Based on markers of the first instrument mapped in the 2D x-ray recordings, at least two reference lines are defined restricting the specific point. A second interventional instrument is inserted in the region of the specific point. Fluoroscopy images of the vessel with the second instrument are obtained by adjusting the x-ray device. The reference lines in the fluoroscopy images are superimposed as localization aid. The specific point in the vessel can also be restricted by a reference region as a localization aid defined based on x-ray recordings of the specific point obtained using contrast agent.

5 Claims, 3 Drawing Sheets

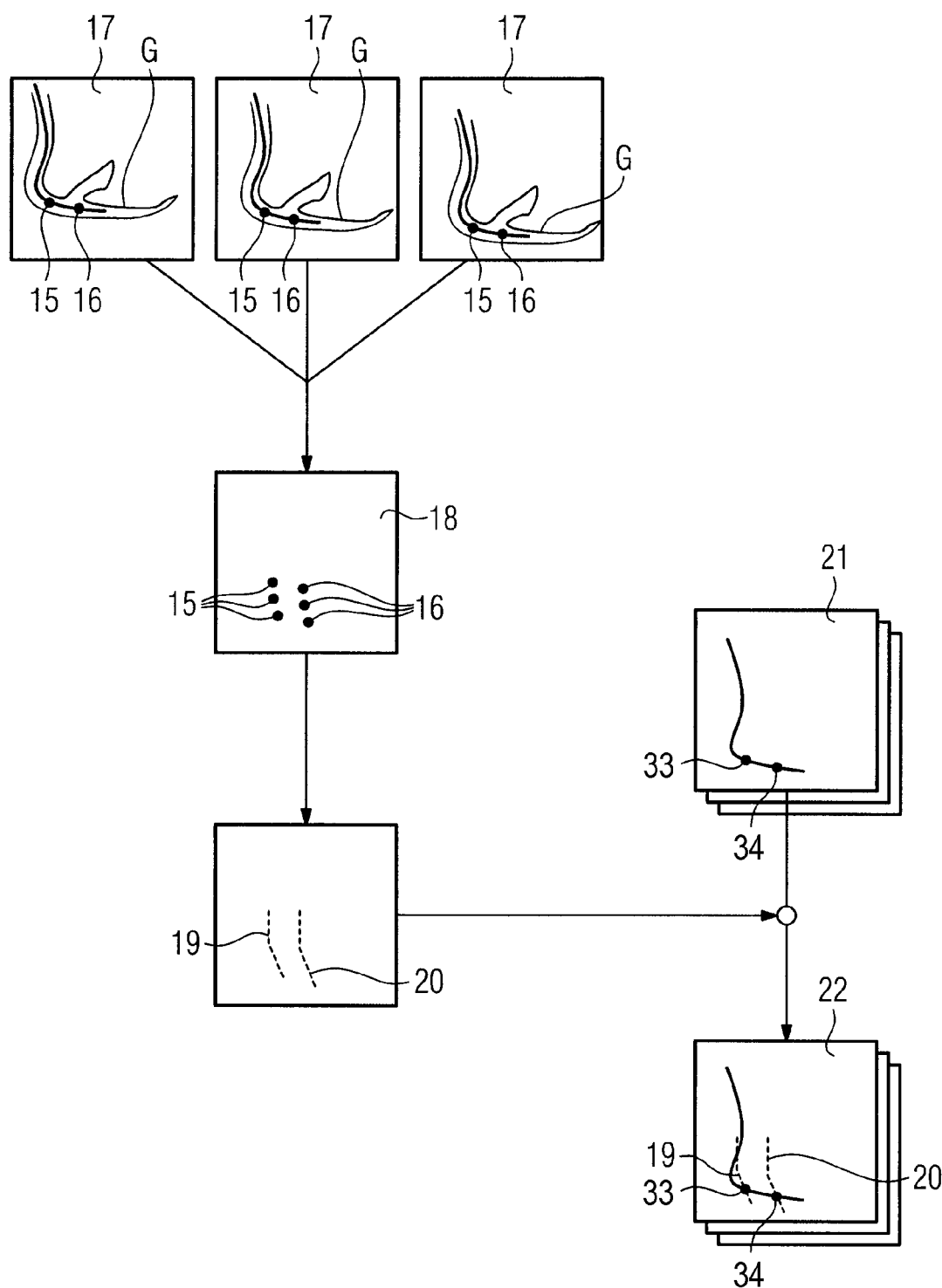

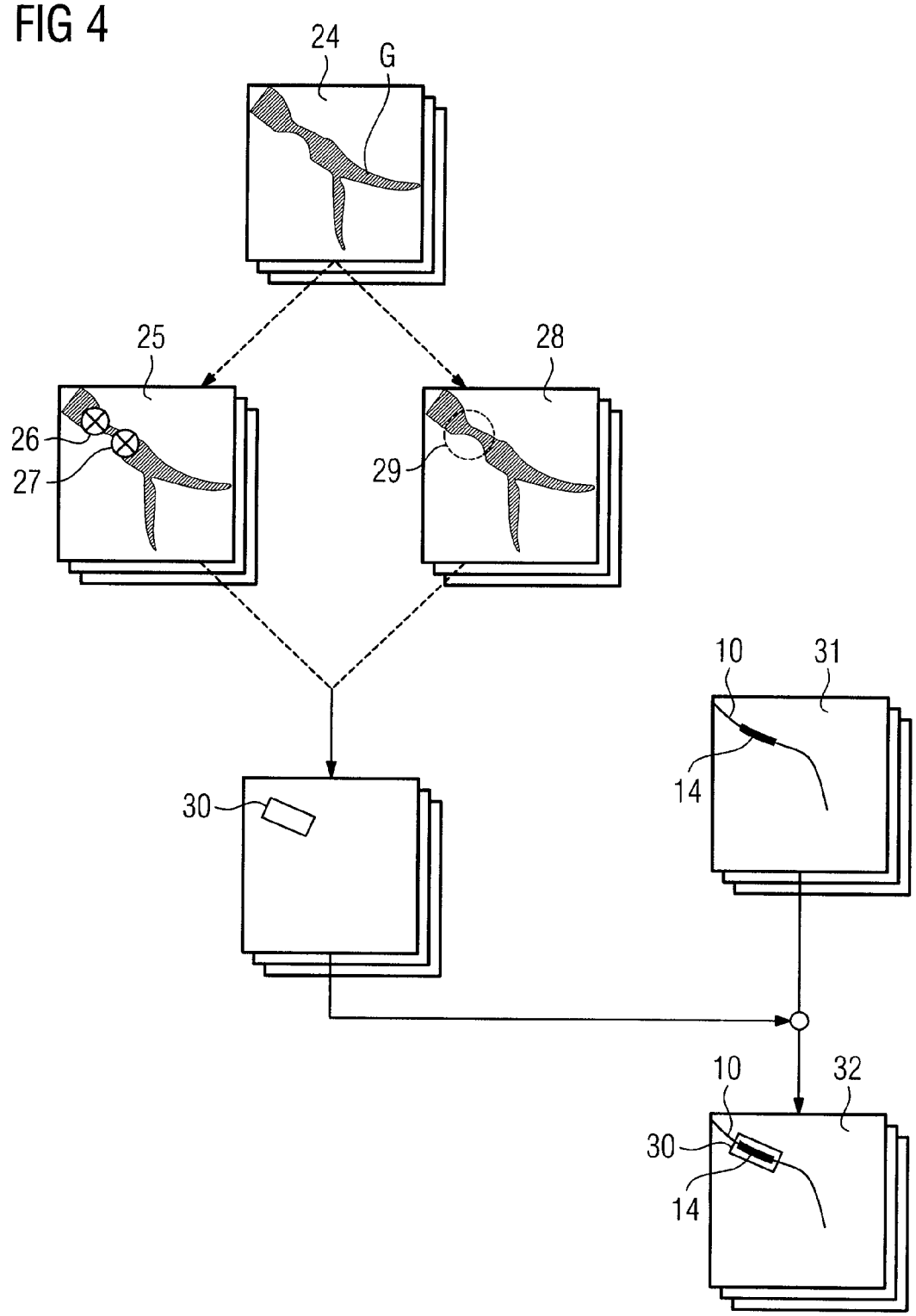

APPARATUS FOR ASSISTING WITH THE POSITIONING OF AN IMPLANT

CROSS REFERENCE TO RELATED APPLICATIONS

This application claims priority of German application No. 10 2009 016 482.0 filed Apr. 6, 2009, which is incorporated by reference herein in its entirety.

FIELD OF THE INVENTION

The invention relates to an apparatus for assisting with the positioning of an implant on a specific point in a vessel of a patient using a minimally-invasive intervention.

BACKGROUND OF THE INVENTION

In the case of minimally-invasive interventional interventions in radiology, cardiology and neurosurgery, different interventional instruments are used, which can comprise for instance a balloon for extending a vessel, a stent for eliminating a vessel stenosis or a prosthesis etc. The positioning of an interventional instrument on a specific point in the body of a patient during the minimally-invasive intervention very frequently takes place using x-rays. Attempts are made here to work with as small an x-ray dose as possible so as to keep the patient's and medical personnel's radiation exposure to a minimum. The visibility of the interventional instrument is however becoming increasingly more difficult not only on account of the use of ever smaller x-ray doses but also since the materials used for the interventional instruments are becoming increasingly more transparent for x-rays and it is always preferred by the average patient.

For a successful intervention, an exact positioning of an interventional instrument on the provided point is however necessary. This is particularly difficult in interventional cardiology, since the target vessel point is generally constantly moving as a result of the heart beat and frequently has to be processed using rather unfavorable projection directions when recording the x-ray images for guiding and positioning the interventional instrument.

SUMMARY OF THE INVENTION

The object underlying the invention is therefore to specify an apparatus of the type cited in the introduction such that the positioning of an interventional instrument on a certain point in a vessel is facilitated.

This object is achieved in accordance with the invention by an apparatus for assisting with the positioning of an implant on a specific point in a vessel of a patient using a minimally-invasive intervention, comprising an x-ray device, a first interventional instrument with two x-ray positive markers, between which is located a functional element, a second interventional instrument including an implant and a computing facility. The invention is based on the consideration that a series of 2D x-ray recordings is obtained of the vessel provided with the interventional instrument in the case of a first interventional instrument inserted in the region of the specific point of the vessel when specifically adjusting the x-ray device relative to the patient, particularly if the functional element of the first interventional instrument is positioned in the region of the specific point. Based on the markers of the first interventional instrument imaged in the 2D x-ray recordings, the computing facility can determine at least two reference lines, which limit the specific point. Here the images of the first and the second markers are in each instance identified in different sequentially recorded x-ray recordings and a connecting line is laid by the images of the first marker and the images of the second marker in each instance so that a first and a second reference line are produced. In order to position the implant, fluoroscopy images of the vessel provided with the second interventional instrument are finally obtained with the second interventional instrument inserted in the region of the specific point of the vessel by using the same adjustment of the x-ray device relative to the patient, in which the reference lines, as orientation aids, are superimposed in order to position the implant on the specific point in the vessel with the aid of the computing facility.

The two reference lines therefore limit the specific point of the vessel, on which the implant is to be positioned, so that the positioning of the implant is facilitated with the aid of fluoroscopy images. The use of the apparatus is particularly suitable if the specific point of the vessel is a stenosis for instance, which is initially extended with a balloon as a functional element of the first interventional instrument, with the reference lines being determined. The reference lines can then be used for positioning a stent as an implant of the second interventional instrument.

The determination of the reference lines can also take place here by moving the specific point of the vessel, i.e. the reference lines are generated so that they detect and/or map the movement, generally the periodic movement of the specific point of the vessel. The reference lines therefore generally do not run straight.

The superimposition of the reference lines in the fluoroscopy images is possible without further image registration, since the adjustments of the x-ray device are not changed when recording the 2D x-ray recordings and the fluoroscopy images. The intensity of the x-rays may only be higher when obtaining the 2D x-ray recordings, in order to increase the visibility of the markers of the first interventional instrument.

An embodiment of the invention provides for the reference lines to be superimposed into the fluoroscopy images as stationary extremes. The reference lines are in this way fixedly and/or statically superimposed in the fluoroscopy images. The determination of the extremes preferably takes place such that the specific point in the vessel is always located within the two reference lines, even if the specific point of the vessel moves periodically into the fluoroscopy images.

The object of the present invention is also achieved by an apparatus for assisting with the positioning of an implant on a specific point in a vessel of a patient using a minimally-invasive intervention, comprising, an x-ray device, an interventional instrument comprising an implant and a computing facility. Based on x-ray recordings obtained of the vessel when using contrast agent in the case of a specific adjustment of the x-ray device relative to the patient, the specific point of the vessel is identified, marked with the aid of the computing facility and a reference region is defined, which limits the specific point. If the interventional instrument is inserted into the body of the patient in the region of the specific point of the vessel, fluoroscopy images of the vessel provided with the interventional instrument can be obtained while at the same time adjusting the x-ray device relative to the patient, in which the 2D x-ray recordings were obtained, into which fluoroscopy images the reference region is superimposed with the aid of the computing facility. The specific point of the vessel can therefore also be identified, marked and/or characterized in this way, as a result of which the exact positioning of the implant is facilitated.

According to a variant of the invention, the start and end of the specific point is marked to identify the specific point in one or several 2D x-ray recordings, which can take place by means of manual inputs, mouse clicks, touch panels or even in an automated fashion by means of corresponding pattern recognition software. Alternatively, a region of interest, which may be identical to the reference region and comprises the specific point can also be determined for marking the specific point.

An embodiment of the invention provides for the apparatus to have a facility for determining a periodic movement of the specific point of the vessel, in order to be able to take into account a periodic movement of the specific point when superimposing the reference region into the fluoroscopy images. The facility is preferably an ECG device, in order to detect periodic movements of the specific point of the vessel produced as a result of periodic heart movements.

The reference region can in turn be superimposed into the fluoroscopy images as a stationary reference region. Alternatively, only a fluoroscopy image of the specific point in the vessel is then recorded and the reference region is superimposed into the respective fluoroscopic image, if the specific point in the vessel is in the same movement phase, in respect of which the reference region was determined. The reference region is therefore determined using the ECG of the patient only in respect of a specific movement phase, during which fluoroscopy images are subsequently obtained, into which the reference region is superimposed. This reduces the x-ray dose for the patient and the medical personnel.

BRIEF DESCRIPTION OF THE DRAWINGS

Exemplary embodiments of the invention are shown in the appended schematic drawings, in which;

FIG. 3 shows an illustration of the definition and superimposition of reference lines in fluoroscopy images and FIG. 4 shows an illustration of the definition and superimposition of a reference region in fluoroscopy images.

DETAILED DESCRIPTION OF THE INVENTION

Figure 1:
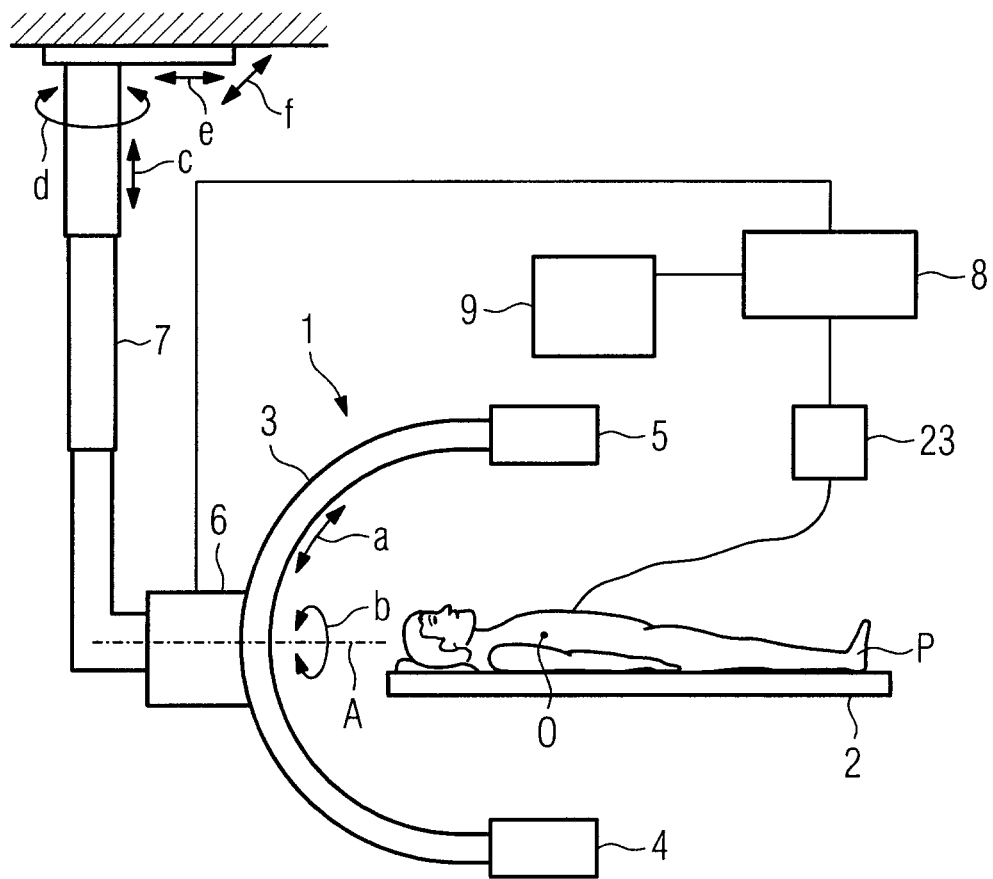
FIG. 1 shows an x-ray facility for assisting with a minimally-invasive intervention on a patient.

In the case of the present exemplary embodiment of the invention, the x-ray facility shown in FIG. 1 for assisting with a minimally-invasive intervention on a patient P has a C-arm x-ray device 1 and a schematically illustrated patient couch 2. The patient P which has a stenosis in a coronary blood vessel (not shown in FIG. 1) is positioned on the patient couch 2. The stenosis is to be provided with a stent by using the x-ray facility so as to keep the vessel stenosis of the coronary blood vessel open for the blood flow.

With the C-arm x-ray device 1, image information from inside the body of the patient P is obtained in order to guide and position the stent. To this end, the C-arm x-ray device 1 includes inter alia a C-arm 3, on which an x-ray source 4 and an x-ray detector 5 are arranged opposite to one another.

The C-arm 3 is adjustably mounted on a support 6 about its orbital axis O in the directions of the double arrow a. In the case of the present exemplary embodiment, the support 6 is arranged on a ceiling stand 7, which provides the adjustment possibilities identified in FIG. 1 with double arrows c, d, e and f of the support 6 provided with the C-arm 3. The C-arm 3 is also adjusted with the support 6 about its angulation axis A in the directions of the double arrow b.

In a manner known per se, the C-arm x-ray device 1 enables 2D x-ray projections or fluoroscopy images of the patient P mounted on the patient couch 2 to be recorded from different projection directions, which can be displayed on a viewing device 9 connected to an image computer 8.

Figure 2:
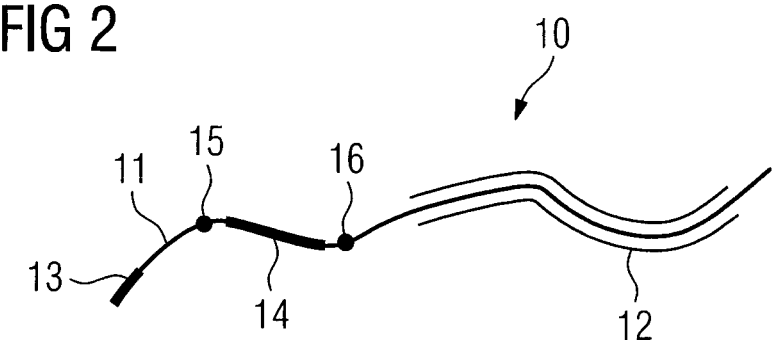
FIG. 2 shows an interventional instrument.

In the case of the present exemplary embodiment of the invention, two interventional instruments are provided, in order to correctly position the stent in the narrowed point in the coronary blood vessel. FIG. 2 shows the basic design of the interventional instrument.

In the case of the present exemplary embodiment of the invention, an interventional instrument 10 includes a catheter 12 provided with a guide wire 11. The guide wire 11 has a tip 13 and a functional element 14. The guide wire 11 has a first x-ray positive marker 15 and a second x-ray positive marker 16 upstream and downstream of the functional elements 14 in each instance. The two interventional instruments differ from one another such that the functional element 14 of the first interventional instrument is a balloon for extending the narrowed point of the coronary blood vessel and that the functional element 14 of the second interventional instrument is an implant in the form of a stent for the arrangement in the narrowed point of the coronary blood vessel.

To assist with the positioning of the stent, the C-arm 3 is moved into a suitable position relative to the patient P by pivoting about its orbital axis O and/or its angulation axis A, in which position 2D x-ray recordings and fluoroscopy images of the coronary blood vessel comprising the narrowed point can be obtained. This position of the C-arm 3 and incidentally also the other adjustments of the C-arm x-ray device 1, such as collimation, tube voltage etc. remain unchanged for the further positioning of the stent.

The first interventional instrument, in other words the catheter 10 with the guide wire 11, which has the balloon as the functional element, is firstly minimally-invasively inserted into the body of the patient P by way of a leg vein for instance and is moved towards the heart of the patient P. If the markers 15, 16 and the balloon are in the region of the narrowed point of the coronary heart vessel G, the balloon is introduced into the narrowed point of the coronary heart vessel G with the aid of the x-ray positive markers 15, 16 using x-ray control. Several 2D x-ray recordings, which are generally fluoroscopy images 17, are obtained here, as shown in FIG. 3, in which the markers 15 and 16 are mapped. The images of the markers 15 and 16 in the fluoroscopy images 17 are either identified here manually, for instance by means of a computer mouse connected to the image computer 8 or by means of a touchscreen, or automatically by means of pattern recognition software and are extracted from the fluoroscopy images. An image sequence 18 for images of the marker 15 and images of the marker 16 result herefrom. If the images of the marker 15 and the images of the marker 16 are then connected in each instance to a connecting line, a first reference line 19 developed from the images of the marker 15 and a second reference line 20 developed from the images of the marker 16 are obtained in each instance. As, during the arrangement of the balloon, the reference lines 19, 20 were generated in the narrowed point of the coronary heart vessel G, they restrict the narrowed point of the coronary heart vessel G and/or mark the narrowed point of the coronary heart vessel G.

If, after the widening of the narrowed point of the coronary heart vessel G with the balloon, the first interventional instrument is removed from the body of the patient and the second interventional instrument, which has a first x-ray positive marker 33 and a second x-ray positive marker 34 and the stent as a functional element, is minimally-invasively inserted into the body of the patient P and moved toward the heart of the patient using x-ray control, the reference lines 19 and 20 can be superimposed into the currently obtained fluoroscopy images 21 without further image registration, since the recording parameters, such as projection direction, tube-detector distance, distance of the x-ray beam source 4 and of the x-ray beam detector 5 from the patient etc. of the C-arm x-ray device 1 remain unchanged, and therefore identical. The images 22 result by superimposing the currently obtained fluoroscopy images 21 with the reference lines 19, 20, said images 22 enabling the doctor implementing the intervention to easily locate the exact positioning of the stent in the narrowed point of the coronary heart vessel G.

In the case of the present exemplary embodiment of the invention, the vessel comprising the narrowed point is a coronary heart vessel G, which moves periodically as a result of the heart beat. As the reference lines 19, 20 were determined on the basis of fluoroscopy images, which have the periodic movement of the narrowed point of the coronary heart vessel G in its sequence, the determined reference lines 19, 20, which run in a curvilinear fashion, also contain the movement of the narrowed point of the coronary heart vessel G. The representation of the reference lines 19, 20 shown in FIG. 3 is therefore a simplified representation.

The reference lines 19, 20 can finally be superimposed in the fluoroscopy images 21 as fixed reference lines 19, 20 and if necessary only after a scaling. The reference lines 19, 20 are in this case extremes, i.e. the reference lines 19, 20 are superimposed in this way into the currently recorded fluoroscopy images 21, such that the narrowed point of the coronary heart vessel G is always within the two reference lines 19, 20, even with a periodic movement of the narrowed point of the coronary heart vessel G.

A further exemplary embodiment of the invention is illustrated with the aid of FIG. 4. Contrary to the previously described exemplary embodiment of the invention, with this embodiment a contrast agent is applied into the coronary vessel of the patient P after adjusting the C-arm x-ray device 1 relative to the patient P. 2D x-ray recordings, generally fluoroscopy recordings 24, are then obtained of the narrowed point of the coronary heart vessel, and the narrowed point in the fluoroscopy images is identified again manually or automatically. The narrowed point can be identified here in a fluoroscopy image 25 with its starting point 26 and end point 27 or in a fluoroscopy image 28 as "region of interest 29". A reference region 30 is determined based on this identifier, said reference region restricting the narrowed point and also possibly being identical to the "region of interest 29".

In the next step, as described above, the interventional instrument comprising the stent is inserted minimally-invasively into the body of the patient P and moved toward the heart of the patient P, in particular to the narrowed point of the coronary heart vessel G. As a result of the unchanged adjustment of the C-arm x-ray device 1, the defined reference region 30 can be easily superimposed into the currently recorded fluoroscopy images 31 of the narrowed point of the coronary heart vessel G without further registration, so that images 32 are produced as in FIG. 4.

Contrary to the case of the first exemplary embodiment of the invention, the defined reference region does not automatically take into account the periodic movement of the narrowed point of the coronary heart vessel G. To achieve this, in the case of the second exemplary embodiment of the invention, an ECG device 23 is provided, with which an ECG of the patient P can be determined in parallel with the recording of fluoroscopy images. It is now possible to define the reference region 30 only with the aid of fluoroscopy images, which were recorded at a certain movement phase of the heart and/or the narrowed point of the coronary heart vessel G. If the interventional instrument comprising the stent is inserted into the body of the patient and moved toward the narrowed point, fluoroscopy images 31 are then only recorded of the narrowed point of the coronary heart vessel G and the reference region 30 is superimposed if the narrowed point of the coronary heart vessel G is in the same movement phase, in respect of which the reference region 30 was defined. The periodic movement of the narrowed point can in this way be taken into account during the superimposition of the reference region 30.

There is alternatively also the possibility of superimposing the reference region 30 into all recorded fluoroscopy images 31 as a fixed reference region 30 or if necessary only after a scaling. The reference region 30 is in this case also to be seen as an extreme, so that this is always located within the reference region 30 irrespective of the movement of the narrowed point of the coronary heart vessel G.

Contrary to the described exemplary embodiments of the invention, an ECG device does not necessarily have to be used to determine the periodic heart movement. A movement sensor arranged on the body surface can also be used to detect the periodic heart movement for instance.

The movement of the vessel can incidentally also be produced by breathing. A corresponding breathing monitor can be provided to detect the breathing movement.

The superimposition of the reference lines and/or reference region can incidentally also take place if a zoom is performed to achieve a higher image resolution based on the fluoroscopy images. As the zoom conditions are known, the superimposition of the reference lines and/or the reference region can be performed accordingly.

The invention claimed is:

1. An apparatus for assisting positioning of an implant on a specific point in a vessel of a patient using a minimally-invasive intervention, comprising:
   a first interventional instrument with a first set of two x-ray positive markers and a functional element located between the first set of the two x-ray positive markers that is inserted in a region of the specific point of the vessel;
   a second interventional instrument with a second set of two x-ray positive markers and the implant located between the second set of the two x-ray positive markers that is inserted in the region of the specific point of the vessel;
   an x-ray device that is adapted to record:
      a first series of 2D x-ray recordings of the vessel comprising the first interventional instrument by adjusting the x-ray device relative to the patient,
      a second series of fluoroscopy images of the vessel comprising the second interventional instrument by adjusting the x-ray device relative to the patient; and
   a computer that is adapted to:
      define at least two reference lines based on the first set of the two markers by connecting instances of one of the first set of the two markers to each other and instances of the other of the first set of the two markers to each other imaged in the first series of 2D x-ray recordings for restricting the specific point,
      superimpose the reference lines defined in the first series of the 2D x-ray recordings into the second series of fluoroscopy images.

2. The apparatus as claimed in claim 1, wherein the computer is further adapted to superimpose the reference lines into the second series of fluoroscopy images as fixed extremes.

3. A method for assisting positioning an implant on a specific point in a vessel of a patient using a minimally-invasive intervention, comprising:
   inserting a first interventional instrument with a first set of two x-ray positive markers and a functional element located between the first set of the two x-ray positive markers in a region of the specific point of the vessel;

recording a first series of 2D x-ray recordings of the vessel comprising the first interventional instrument by adjusting an x-ray device relative to the patient;

removing the first interventional instrument from the region of the specific point of the vessel;

inserting a second interventional instrument with a second set of two x-ray positive markers and the implant located between the second set of the two x-ray positive markers in the region of the specific point of the vessel;

recording a second series of fluoroscopy images of the vessel comprising the second interventional instrument by adjusting the x-ray device relative to the patient;

defining at least two reference lines based on the first set of the two markers by connecting instances of one of the first set of the two markers to each other and instances of the other of the first set of the two markers to each other imaged in the first series of 2D x-ray recordings for restricting the specific point by a computer; and superimposing the reference lines defined in the first series of 2D x-ray recordings into the second series of fluoroscopy images by the computer.

4. The method as claimed in claim 3, further comprising identifying a start and an end of the specific point.

5. The method as claimed in claim 3, further comprising identifying an area of interest comprising the specific point for marking the specific point.

* * * * *